United States Patent [19]

Koocher

[11] 4,380,587
[45] Apr. 19, 1983

[54] FILM BADGE FOR DETERMINING CARBONYL COMPOUNDS

[75] Inventor: Martin Koocher, Lexington, Mass.

[73] Assignee: Arthur D. Little, Inc., Cambridge, Mass.

[21] Appl. No.: 294,584

[22] Filed: Aug. 20, 1981

[51] Int. Cl.$^3$ ..................... G01N 21/75; G01N 31/00
[52] U.S. Cl. ....................................... 436/128; 422/57;
422/58; 422/83; 422/88; 436/4; 436/167;
436/902
[58] Field of Search ............ 23/230 R, 232 R, 230 M;
422/55, 56, 57, 58, 83, 88; 436/4, 128, 167, 902

[56] References Cited

U.S. PATENT DOCUMENTS

| 3,642,449 | 2/1972 | Novak et al. | 422/56 X |
| 3,645,696 | 2/1972 | Iannacone et al. | 23/230 M |
| 3,950,980 | 4/1976 | Braun et al. | 422/83 X |

OTHER PUBLICATIONS

Konopczynshi, Chemical Abstracts, vol. 88, 1978, No. 88:140930v.
Browne et al., "Physical and Chemical Methods of Sugar Analysis" John Wiley & Sons, New York, 1941, pp. 665–676.
Knapp, "Handbook of Analytical Derivatization Reactions", John Wiley & Sons, New York, 1979, pp. 338–346.

*Primary Examiner*—Arnold Turk
*Attorney, Agent, or Firm*—Richard J. Hammond

[57] ABSTRACT

Method for the determination of fluidic-contained aldehydes. The method comprises bringing into contact said aldehyde and a chemically inert substrate having adhered to the surface thereof a substantially monodisperse system of particles of a derivatizing agent for the aldehydes thereby forming nucleating crystals; treating said nucleating crystals with a metastable supersaturated solution in which said nucleating crystals can grow; growing said nucleating crystals to form an optically measurable film of crystals; and optically measuring said film of crystals to determine the concentration of fluidic-contained aldehydes.

10 Claims, 7 Drawing Figures

FILM BADGE FOR DETERMINING CARBONYL COMPOUNDS

The present invention relates to a method for determining aldehydes contained in fluids, more particularly, to a method for the determination of fluidic-contained aldehydes wherein such aldehydes contact a derivitizing agent and by treatment with a crystal growing solution, form crystals susceptible to optical measurement. A film badge for such determination is useful in such method.

Concern over air-borne contaminants in work or home environments has increased rapidly. Employers, employees as well as various government agencies alike now recognize more clearly the link that exists between disease and air that is breathed in the work place. Similar hazards have been noted in homes and private dwellings. In an attempt to provide a measure of exposure control in areas where potential hazards, air (or water) polutants may be present, methods have been developed where exposure to harmful materials can be identified or monitored. These methods make it possible to analyze a fluid, air, water, etc. in any environment for numerous toxic substances, such including vinyl chloride, benzene, toluene, xylenes, acetone, etc.

The original method for monitoring exposure was a portable pump and tube apparatus. This technique is still in use today. Personal monitoring gradually evolved from this inconvenient and cumbersome apparatus to the newer, less expensive, film badge vapor monitors. These monitors simply require wearing near the breathing zone and, based on diffusion, provide a method of measuring the time-weighted average concentration of hazardous vapors to which the wearer is exposed. An example of such vapor detection device is U.S. Pat. No. 3,714,562 issued on McNerny which discloses the use of a metallic film to absorb a selected vapor, the presence of the vapor being measured by a change in resistance of the film. Other resistance-type sensing systems are disclosed in U.S. Pat. Nos. 3,703,696 and 3,950,980. A further detection system is disclosed by Palmes and Gunnison, "Personal Monitoring Device For Gaseous Contaminants" American Industrial Hygiene Association Journal, 34 (#2) February, pp 78-81 (1973). This device measures vapor concentration by determining the quantity of a selected gas which diffuses through a single orifice of known size into a chamber maintained at zero concentration of the selected gas by means of a collecting medium. While the devices themselves are lightweight, portable and simple of manufacture, the process required to identify or quantify the vapor exposure require the sophistication and expense of a well equipped analytical laboratory. A high degree of skill is required to effectively operate such facility.

Further the majority of commercially available monitors are not capable of determining the vapor concentrations of the most commonly used, pervasive toxicants, the aldehydes.

It is therefore an object of the present invention to provide a simple and inexpensive method for determining the concentration of liquid or gaseous-contained aldehydes.

It is a further object of the present invention to provide a method for determining the concentration of fluidic contained aldehydes which is sensitive and accurate and eliminates excessive or complicated sample analysis means.

It is an additional object of the present invention to provide a detection method which is simple to perform and which may be suitable for on-site use, requiring, in some cases, no apparatus or equipment beyond that supplied in a small test kit or simple test device.

A still further object of the present invention is to provide a detection method designed to require only currently available optical apparatus, e.g., spectrophotometer, in those cases where visual measurement is not sufficient.

It is an additional object of the present invention to provide a simple inexpensive detection equipment which is suitable for on-site use and which may not require a skilled technician to obtain accurate analytical results.

According to the principles of the invention there is provided a method for determining fluidic-contained aldehydes comprising the steps bringing into contact a chemically inert substrate having adhered to the surface thereof a substantially monodisperse system of particles of a derivitizing agent for said aldehydes with the fluidic contained aldehydes, thereby forming nucleating crystals. These nucleating crystals are then treated with a metastable, supersaturated solution in which the nucleating crystals can grow and by such treatment the nucleating crystals grow to a size and extent that an optically measurable film of crystals results. The concentration of aldehyde (represented by the film of crystals) during the time of exposure is measured by an optical measuring technique. As a further embodiment of the present invention, there is provided a film badge for measuring the presence or time-average amounts of fluidic-contained aldehydes which comprises a chamber that encloses a substrate layer having adhered to the surface thereof a substantially monodisperse system of particles of a derivitizing agent for said aldehyde and a porous fluid-flow attenuating layer superimposed on the cavity and substrate layer.

For a more complete understanding of the nature and objects of the present invention reference should be made to the following detailed description taken in connection with the accompanying drawings, in which.

The method of the present invention is concerned with detecting or monitoring the amount of hazardous material e.g., aldehydes in a fluid (gas or liquid) by bringing the aldehyde-containing fluid into contact with an inert substrate that has adhered thereto a substantially monodisperse system of a derivatizing agent for aldehydes. The derivatizing agent is of particle size in the micron to submicron range and, as such, on contact with the aldehyde-containing fluid reacts with the aldehyde, forming a derivative crystal also of micron to submicron dimensions that behaves, in the next reaction step, as a nucleating site for crystal growth. In order to effect such growth, the inert substrate material having the derivatizing nucleating sites therein is immersed in a metastable/supersaturated solution molecularly identical to the aldehyde-derivatizing agent reaction product. Acting in the classical manner, the nucleating (derivatized aldehyde) sites provide centers of growth for the supersaturated compounds, the number of crystals grown, their size and their density (i.e., the number of crystals per unit area), being a function of the number of nucleating sites, which, are a function of the number of molecules of aldehyde contacting the monodisperse system of derivatizing particles.

In this case, the grown crystals are, of course, substantially chemically homogeneous.

THE SUPERSATURATED META STABLE SOLUTION

The degree of supersaturation of the solution from which the crystals are formed is an important factor governing their size and number. In general, if the solution is rendered markedly metastable, a relatively large quantity of crystalline material will be formed in an attempt to relieve (stabilize) the solution. If, however, the saturation point is barely passed, crystal formation will be disadvantageously gradual, taking excessive periods to grow from the nucleating sites.

Figure 1:
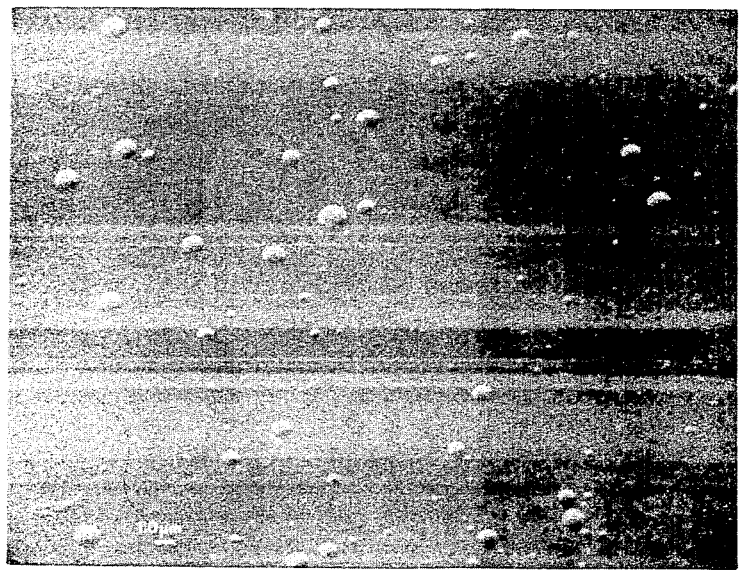
FIG. 1 is an electron microscope photograph of the substantially monodisperse system of particles of derivatizing agent.
Figure 2:
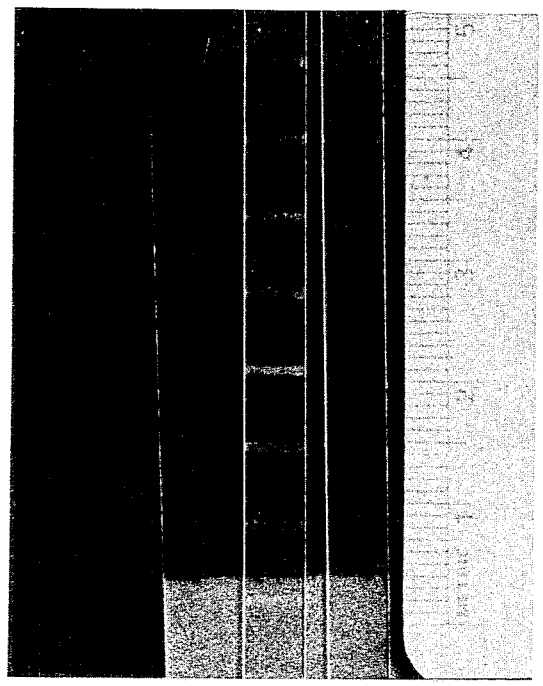
FIG. 2 is a photograph of two film strips exposed to 7.5 ppm formaldehyde gas (left strip) and 0.75 ppm formaldehyde gas (right strip).
Figure 3:
FIG. 3 is a photograph (300×) of the crystals grown by the method of the present invention after contact with 7.5 ppm gaseous formaldehyde.
Figure 4:
FIG. 4 is a photograph (300×) of the crystals grown by the method of the present invention after contact with 0.75 ppm gaseous formaldehyde.

Significantly, the number of nuclei formed, i.e. the number of derivatized nucleating sites, determines the ultimate size of the grown crystals since the amount of material separating from the metastable solution is divided among the sites. The crystal size will increase to a maximum with increasing degree of metastability. Under constant supersaturated metastable conditions, with few nucleating sites, crystallization will occur about a few centers resulting in relatively large crystals (FIG. 4). Where many derivatized sites are present, a large number of very small crystals are formed (FIG. 3). Further, since the habit of a crystalline substance is affected by external conditions, e.g., the rate of deposition, slower deposition (from super saturation barely past the saturation concentration) produces a crystalline lattice whose crystal face is essentially flat. The more rapid depositions tend to build up the crystal face toward an irregular point. Light is scattered more radily from the irregular and pointed crystals, i.e., they are more "visible".

The solution of use herein to produce the grown crystals from the derivatized nuclei is a metastable supersaturated one, i.e., a supersaturated solution in which spontaneous cystallization is improbable, although a crystal placed in such metastable solution will grow. In addition to metastability, the supersaturated solution must also be formed of the derivatized aldehyde (the compound to be detected). For example, if the aldehyde to be detected or determined is formaldehyde, a derivatizing agent for such would be phenyl hydrazine. The metastable, supersaturated solution is therefore formed from a solution, preferably aqueous, of formal phenylhydrazone. By using such solutions rapid crystal growth occurs (within 1 or 2 minutes and no longer than 60 minutes). The result being a homogeneous nucleation of the crystal growth of formal phenylhydrazone.

Various other derivatized compounds for forming the supersaturated metastable solutions are useful herein and are particularly exemplified in the specification under the heading "Derivatizing Agents".

THE DERIVATIZING AGENTS

The derivatizing compounds capable of providing nucleating crystals upon contact with fluidic-contained aldehydes are those commonly recognized as useful in the preparation of derivatives suitable for the characterization of aldehydes. It should be noted, however, that a large number of these derivatizing agents are also useful for the characterization of ketones, ketoesters, ketoacids and many other compounds possessing the carbonyl group including the isocyanates. Hence, while this invention is particularly concerned with the qualitative and quantitative aspects of aldehyde determination, such can also be successfully applied in the analysis of these other carbonyl compounds. The following of compounds are reactive with aldehydes to produce the nucleating sites useful in the present invention: 2,4-Dinitrophenylhydrazine; Semicarbazide; Dimethone or Dimedone; p-Nitrophenylhydrazine; Phenylhydrazine; Thiosemicarbazide; Oximes; Bromobenzohydrazine (o,m,p); 2,4-Dinitromethylphenylhydrazine; p-Carboxyhenylhydrazine; Nitrobenzenesulfonhydrazine; Nitrobenzohydrazine; Diphenylhydrazine 2-Naphthylhydrazine; p-Chlorobenzohydrazine; m-Chlorobenzohydrazine; Nitroguanylhydrazine; $\alpha$-($\alpha$,4-Nitrophenyl)-$\alpha$-methylhydrazine; Xenylsemicarbazide; Tolylsemicarbazide (o,m,p); Phenylsemicarbazide; 1-Naphthylsemicarbazide; 2-Naphthylsemicarbazide; 3,5-Dinitrophenylsemicarbazide; Dibromomethone; Benzothiazole; Benzothiazoleine; Hydantoins; Aminomorpholines; Hydrazinobenzoic acid, 5-(1-Phenylmethyl)semioxazide; 1,3-Cyclohexadione; 1,2-Bis(p-methoxybenzylamino)ethane; adipic dihydrazide; benzoylhydrazine, isonicotinic acid hydrazide; nicotinic acid hydrazide; oxalyl dihydrazide; oxamic hydrazide; and salicylhydrazide.

The preferred derivatizing agents for the method of the present invention are p-hydroxybenzoic acid hydrazide, 2,4-dinitrophenylhydrazine, semicarbazide, dimethone, p-nitrophenylhydrazine, phenylhydrazine and thiosemicarbazide. Particularly preferred is p-hydroxybenzoic acid hydrazide.

THE NUCLEATING SITES

As noted earlier, the inert substrate has adhered to its surface the here-in-above derivatizing agents in the form of a monodisperse system of particulated derivatizing agent. The monodispersion is a group of micron or submicron particles, preferably ranging between about 0.01 $\mu$m to 1.0 $\mu$m. The term "monodispersed system" as used herein is intended to mean a collection of particles which are substantially of the same size having, on the substrate, a relatively uniform spacing between them. When contacted with the fluidic-contained aldehyde, a reaction occurs which essentially changes the chemical identity of the dervatizing agent to that of a derivatized aldehyde. It is the derivatized aldehyde (also of micro or submicron particle size) that behaves as the nucleating site for crystal growth from the metastable/supersaturated solution discussed above. While the actual size of the grown crystals varies considerably depending on the factors disclosed earlier; see the Supersaturated Metastable Solution, the usefulness of this method lies in optically, preferably visually being able to identify these crystals and establish their number (density) by such optical determination. FIG. 4, for example, depicts the relatively large derivatized crystals encountered at low concentrations of aldehyde.

These crystals are in the range of 8–10μ. FIG. 3, shows the small, but densly clustered derivatized crystals arising from contact with much higher amounts of aldehyde. These crystals range in size from about 3 to 5μ. The practical, useful range, i.e., without the necessity of employing highly sophisticated measuring tools, of grown crystals for any on-site analytical procedure is about from 0.5 to 50μ.

Although the derivatizing agent will normally be a compound which reacts with the fluid-contained aldehyde to form nucleating crystals of the same compound with which the developing solution is supersaturated, this is not necessary providing the nucleating crystals can effectively grow in the supersaturated solution to give an opaque film of crystals which are optically measurable. This phenomenon, called isomorphic crystallization, is well recognized in the art.

The sensitized substrate is conveniently prepared by directing an aerosol of a solution of the derivatizing agent against the surface of the substrate. By maintaining very accurate control over the reagent concentration in the aerosol over the time the aerosol contacts any one area of the surface it is possible to deposit an accurately controlled amount of the derivatizing agent on the substrate. To attain satisfactory adherence of the aerosol particles to the film surface it is desirable, but not necessary, to pretreat the surface, e.g., by application of an electrostatic charge and/or heating the aerosol. Equipment for forming the aerosol particles within the desired size range is commercially available, e.g., a fluid atomization aerosol generator manufactured by Thermo Systems, Inc., such equipment being readily adaptable to making continuous sensitized webs from which film substrates may be cut in any desired size and configuration.

Figure 5:
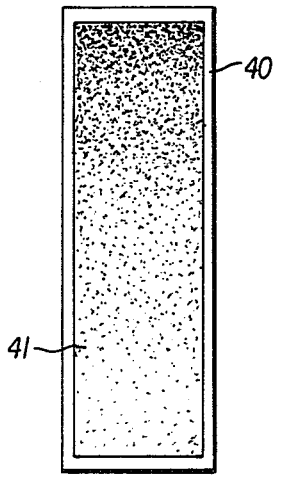
FIGS. 5-7 are illustrations of three forms of film bearing the derivatizing agent and used in forming the grown crystals.
Figure 6:
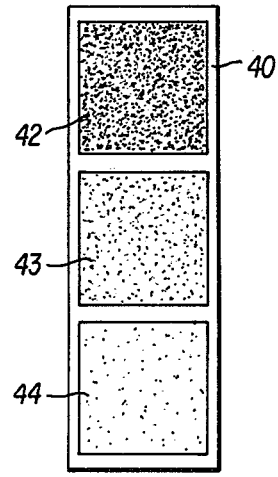
Figure 7:
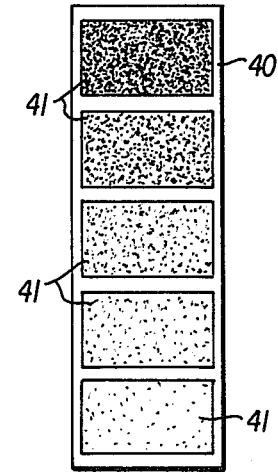

As illustrated in FIGS. 5–7, the sensitized film 40 may be formed to have the concentration of particles 41 of the derivatizing agent essentially uniform over the entire surface; (FIG. 5) or, in discrete steps (FIG. 7) or as shown in FIG. 6, to have the concentration of particles 41 vary in discrete steps 42–44 or through a continuously changing gradient.

According to the mechanism of the basic concept underlying the method of this invention as explained herein above, the quantity of fluidic-contained aldehyde available for reaction with the sensitized film determines the number of nucleating crystals that can be grown when contacted with the metastable supersaturated solution. As noted previously, the developing solution will normally be supersaturated with respect to the reaction product of the aldehyde and derivatizing agent, i.e., with respect to the nucleating crystals, it may, however, be supersaturated with respect to any other crystallizable compound which gives rise to the growth of the nucleating crystals.

Because of the inherent instability of the supersaturated solution, it is usually necessary to prepare it just prior to use. Further, bath stabilizers, such as polyvinylalcohol or polyvinylpyrrolidone are useful in prolonging the effective life of the metastable solution. In performing the developing tests it is normally convenient to have available two prepared reagents, one or both of which is a solution, which when mixed in a given ratio will form a metastable supersaturated solution suitable for contacting the nucleating crystals of the sensitized substrate.

As an alternative to permitting the fluidic-contained aldehydes to contact the entire surface of a sensitized substrate essentially simultaneously, it is possible to direct the aldehydes in a manner to cause reaction with a sensitized substrate which may have the monodispersion deposited as a series of discrete separated areas or as a continuous area having a uniform concentration. This then makes it possible to construct a test device such as a film-badge or a dipstick which may be read in the same manner as a thermometer, the number of developed areas or the height of the final opaque, visible crystals being proportional to the actual concentration of aldehyde to which the sensitized substrate was exposed.

The growth of the nucleating crystals in the metastable supersaturated solution gives rise to an optically observable change. In those cases wherein only an indication of the presence or absence of aldehydes is desired, the creation of a visible or other measurable change is indicative of the presence of aldehydes. In those cases wherein it is required to determine not only aldehyde presence but also concentration, then since the degree of opacity is indicative of concentration, such can be measured by a suitable instrument, e.g., a diffuse reflectance spectrophotometer, or through the use of a calibrated device in which height of column of opacity is a measure of aldehyde concentration. Alternatively, some form of electrical measurement, e.g., film resistance or capacitance, may also be used to determine concentration of the aldehyde.

The coated substrate disclosed herein is particularly useful in the determination of air-borne aldehydes, e.g., formaldehyde, in the work environment. As such, it is conveniently contained in a film badge container which controls the flow of ambient air over the surface of the particles and further acts to protect the substrate from mechanical damage. Film badge containers are well known in the prior art, and take a variety of shapes.

One of the simplest film badges embodiments in which the substrate can be contained is in the form of an elongated sealed container containing at least one passage in the container wall to permit the entrance of ambient air and it subsequent contact and reaction with the derivatizing agent.

U.S. Pat. No. 3,950,980, issued Apr. 20, 1976, incorporated herein by reference discloses a film badge in which the container is comprised of an elongated chamber having superimposed thereon porous fluid flow attenuating layer. By insertion of the coated substrate of this invention, i.e., the substrate having adhered to the surface thereof a substantially nondisperse system of particles of a derivatizing agent for aldehydes, a completed film badge as formed that can be worn by workers who may encounter fluidic-contained aldehydes in the work environment.

As used in the specification and appended claims, the following terms have the meaning indicated: "fluidic-contained aldehydes" is intended to mean both acyclic and cyclic aliphatic and aromatic (carbocyclic and heterocyclic) compounds bearing at least one carbonyl group ($>C=O$) attached to hydrogen, such contained in a gas (an elastic fluid) or liquid (an inelastic fluid). Typical examples of commercially useful aldehydes are formaldehyde, acetaldehyde, benzaldehyde, piperonol, furfuraldehyde and the like.

EXAMPLE 1

Sensitized Film

In forming a sensitized film of submicron particles, 1.0 grams of p-hydroxybenzoic acid hydrazide (Aldrich Chemical Company, catalog No. H2-010-5) is dissolved in 175 ml 0.1 N hydrochloric acid. 0.15 grams oxalic acid dihydrate (Fisher Scientific No. A-219) is dissolved in 425 ml methanol and added to the hydrazide solution. Comparable solutions for forming the sensitized film were prepared without the oxalic acid and the films were found to have comparable sensitivity as those prepared from the solutions having the oxalic acid. However, the incorporation of the oxalate appeared to contribute an added degree of stability to the films. The p-hydroxybenzoic acid hydrazide solution is applied to the substrate film using a fluid atomization aerosol generator (TSI Incorporated Model 9306) and having an aerosol delivery tube (45" long, 1" diameter) containing $3\times0.125$ inch ($7.6\times0.32$ cm) opening. This is a general purpose atomizer based on the Wright Jet Baffle principal and is able to generate both liquid and solid particles. The film base is a 7.5 mil polystyrene. The aerosol is passed through a diffusion dryer prior to entering the aerosol delivery tube. The film is drawn continuously by means of a variable-speed drive motor over a guide roller so that it passes approximately 0.010 inch (0.025 cms) from the aerosol delivery opening. The speed of the film typically is between about 6 inches/minute and 15 inches/minute in this example.

The p-hydroxybenzoic acid particles of FIG. 1 forming the sensitized film surface of this example ranged from about $0.1\mu$ to about $1\mu$ in size.

The films prepared as described above are used to evaluate the presence and/or quantity of formaldehyde vapor to which they have been exposed. As an illustrative test procedure, into an 8"–80 ml test tube is placed an aliquot of a dilute aqueous solution of formaldehyde. Into a second smaller test tube (6"–30 ml) is inserted a strip of the film having been prepared as set forth above. The smaller tube is then inserted within the larger tube, keeping the prepared film from physically contacting the formaldehyde solution. The larger test tube is stoppered and the two test tube assembly allowed to stand a predetermined time.

Using the above procedure, 20 microliters of 30 $\mu$g/ml (approximately 0.6 $\mu$g of formaldehyde) and 20 microliters of 3 g/ml (approximately 0.06 $\mu$g of formaldehyde) of aqueous formaldehyde solutions are placed in each of the two large test tubes. After inserting a strip of the prepared film in each of two smaller test tubes, the tubes were inserted in the larger ones and stoppered. After an overnight period (18 hours) of exposure, the tubes were unstoppered and processed as described below.

Two separate solutions are made up for mixing just before use as the supersaturated developing solution. Solution A is made by adding a 0.4% aqueous solution of p-hydroxybenzoic acid hydrazide in 0.1 N hydrochloric acid to a 1.0% polyvinyl alcohol solution in water. Solution B is a 0.37% aqueous formaldehyde solution (prepared from Fisher Formaldehyde Solution (F-79). These two solutions remained stable for an extended period of time. Mixing of equal quantities of solutions A and B results in a metastable supersaturated solution of formal p-hydroxybenzoic acid hydrazone that is used immediately after formation.

In use, equal volumes of solutions A and B are mixed and poured onto a clean surface. Onto this solution is placed a strip of the film that has been exposed to formaldehyde (as described above), exposure side in contact with the solution. After five (5) minutes of developing, the film is removed, rinsed with water and placed on a clean surface to dry. Positive indication of the presence of formaldehyde appears as the presence of white opaque areas on the transparent background of the film.

The resulting developed films are shown in the figures. FIG. 2 is illustrative of the particle size and density of the crystals obtained in the 0.6 g (about 7.5 ppm) formaldehyde exposure. FIG. 4 represents the exposure to 0.06 g (about 0.75 ppm) of formaldehyde vapor.

It will thus be seen that the objects set forth above, among those made apparent from the preceeding description are efficiently attained and since certain changes may be made in carrying out the above methods and in the compounds set forth without departing from the scope of the invention, it is intended that all matter contained in the above description shall be interpreted as illustrative and not in a limiting sense.

I claim:

1. A method for determining fluidic-contained aldehyde comprising a. contacting a chemically inert substrate having adhered to the surface thereof a substantially monodisperse system of particles of a derivatizing agent for the aldehyde with the fluidic-contained aldehyde to form nucleating sites;

b. treating said nucleating sites with a metastable supersaturated solution in which said nucleating sites can grow;

c. growing said nucleating sites to form an optically measurable film of crystals; and d. optically measuring said film of crystals to determine the concentration of fluidic-contained aldehyde.

2. The method according to claim 1 wherein said chemically inert substrate is a polymeric film.

3. The method according to claim 2 wherein said derivatizing agent for said fluidic-contained aldehyde is adipic dihydrazide; benzoylhydrazine; isonicotinic acid hydrazide; nicotinic acid hydrazide; oxalyl dihydrazide; oxamic hydrazide; salicylhydrazide; 2,4-dinitrophenylhydrazine; semicarbazide; dimethone or dimedone; p-nitrophenylhydrazine; phenylhydrazine; thiosemicarbazide; bromobenzohydrazine (o,m,p); 2,4-dinitromethylphenylhydrazine; p-carboxphenylhydrazine; nitrobenzenesulfonhydrazine; p-nitrobenzohydrazine; diphenylhydrazine; 2-naphthylhydrazine; p-chlorobenzohydrazine; m-chlorobenzohydrazine; nitroguanylhydrazine; $\alpha$-($\alpha$,4-nitrophenyl)-$\alpha$-methylhydrazine; xenylsemicarbazide; tolylsemicarbazide (o,m,p); phenylsemicarbazide; 1-naphthylsemicarbazide; 2-naththylsemicarbazide; 3,5-dinitrophenylsemicarbazide; dibromomethone; benzothiazole; benzothiazoline; aminomorpholines; hydrazinobenzoic acid; 5-(1-phenylmethyl)semioxazide 1,3-cyclohexadione; 1,2-bis(p-methoxybenzylamino)ethane or p-hydroxybenzoic acid anhydride.

4. The method according to claim 3 wherein said sites are 0.01 $\mu$m to 1.0 $\mu$m in size.

5. The method according to claim 1 wherein said supersaturated/metastable solution is an aqueous solution of the fluidic-contained aldehyde reaction product of adipic dihydrazide; benzoylhydrazine; isonicotinic acid hydrazide; nicotinic acid hydrazide; oxalyl dihydrazide; oxamic hydrazide; salicylhydrazide; 2,4-dinitrophenylhydrazine; semicarbazide; dimethone or dimedone; p-nitrophenylhydrazine; phenylhydrazine; thiosemicarbazide; bromobenzohydrazine (o,m,p); 2,4-dinitromethylphenylhydrazine; p-carboxyphenylhydrazine; nitrobenzenesulfonhydrazine; b-nitrobenzohydrazine; diphenylhydrazine; 2-naphthylhydrazine; p-chlorobenzohydrazine; m-chlorobenzohydrazine; nitroguanylhydrazine; α-(α,4-nitrophenyl)-α-methylhydrazine; xenylsemicarbazide; tolylsemicarbazide (o,m,p); phenylsemicarbazide; 1-naphthylsemicarbazide; 2-napthylsemicarbazide; 3,5-dinitrophenylsemicarbazide; dibromomethone; benzothiazole; benzothiazoline; aminomorpholines; hydrazinobenzoic acid; 5-(1-phenylmethyl)semioxazide; 1,3-cyclohexadione; 1,2-bis(p-methoxybenzylamino)ethane or p-hydroxybenzoic acid hydrazide.

6. A film badge useful for determining the presence or time-average amounts of fluidic-contained aldehyde comprising a container having a chamber therein, said chamber enclosing a chemically inert substrate having adhered to the surface thereof a substantially monodisperse system of particles of a derivatizing agent for said aldehyde, the size of said particles being in the micron to submicron range, and superimposed on said chamber and said substrate a porous fluid flow attenuating layer, said porous fluid flow attenuating layer causing the flow of said fluidic-contained aldehyde to contact said substrate layer to form nucleating sites for crystal growth.

7. A method for determining a fluidic-contained carbonyl compound comprising
   a. contacting a chemically inert substrate having adhered to the surface thereof a substantially monodisperse system of particles of a derivatizing agent for the carbonyl compound with the fluidic-contained carbonyl compound to form nucleating sites;
   b. treating said nucleating sites with a metastable supersaturated solution in which said nucleating sites can grow;
   c. growing said nucleating sites to form an optically measurable film of crystals; and
   d. optically measuring said film of crystals to determine the concentration of fluidic contained carbonyl compound.

8. The method of claim 7 wherein said carbonyl compound is selected from the group consisting of ketones, ketoesters, ketoacids and isocyanates.

9. The method of claim 8 wherein the derivatizing agent for said carbonyl compound is adipic dihydrazide; benzoylhydrazide; isonicotinic acid hydrazide; nicotinic acid hydrazide; oxalyl dihydrazide; oxamic hydrazide; salicylhydrazide; 2,4-dinitrophenylhydrazine; semicarbazide; dimethone or dimedone; p-nitrophenylhydrazine; phenylhydrazine; thiosemicarbazide; bromobenzohydrazine (o.m.p.); 2,4-dinitromethylphenylhydrazine; p-carboxyphenylhydrazine; nitrobenzenesulfonhydrazine; p-nitrobenzohydrazine; diphenylhydrazine; 2-naphthylhydrazine; p-chlorobenzohydrazine; m-chlorobenzohydrazine; nitroguanylhydrazine; α-(α,4-nitrophenyl)-αmethylhydrazine; xenylsemicarbazide; tolylsemicarbazide (o.m.p.); phenylsemicarbazide; 1-naphthylsemicarbazide; 2-naphthylsemicarbazide; 3,5-dinitrophenylsemicarbazide; dibromomethone; benzothiazole; benzothiazoline; aminomorpholines; hydrazinobenzoic acid; 5-(1-phenylmethyl)semioxazide; 1,3-cyclohexadione; 1,2-bis(p-methoxybenzylamino)ethane or p-hydroxybenzoic acid hydrazide.

10. The method of claim 9 wherein said nucleating sites at 0.01 μm to 1.0 μm in size.

* * * * *